(12) United States Patent
Smith

(10) Patent No.: US 8,858,431 B2
(45) Date of Patent: Oct. 14, 2014

(54) VAGINAL SPECULUM

(76) Inventor: Michelle Davis Smith, Charleston, SC (US)

(*) Notice: Subject to any disclaimer, the term of this patent is extended or adjusted under 35 U.S.C. 154(b) by 642 days.

(21) Appl. No.: 12/648,810

(22) Filed: Dec. 29, 2009

(65) Prior Publication Data

US 2011/0160540 A1 Jun. 30, 2011

(51) Int. Cl.
*A61B 17/00* (2006.01)
*A61B 1/32* (2006.01)

(52) U.S. Cl.
CPC ........................................ *A61B 1/32* (2013.01)
USPC ............................ 600/220; 600/225; 606/207

(58) Field of Classification Search
USPC ............................ 600/220, 222; 606/205, 207
See application file for complete search history.

(56) References Cited

U.S. PATENT DOCUMENTS

| | | | | |
|---|---|---|---|---|
| 4,615,334 A | * | 10/1986 | Jaeger | 600/195 |
| 4,766,887 A | * | 8/1988 | Cecil et al. | 600/222 |
| 5,072,720 A | * | 12/1991 | Francis et al. | 600/186 |
| 5,179,938 A | | 1/1993 | Lonky | |
| 5,873,820 A | * | 2/1999 | Norell | 600/220 |
| 6,024,696 A | | 2/2000 | Hoftman et al. | |
| 6,379,299 B1 | | 4/2002 | Borodulin et al. | |
| 6,394,950 B1 | * | 5/2002 | Weiss | 600/205 |
| 6,432,048 B1 | | 8/2002 | Francois | |
| 6,595,917 B2 | * | 7/2003 | Nieto | 600/223 |
| 2006/0106416 A1 | * | 5/2006 | Raymond et al. | 606/198 |
| 2008/0114210 A1 | * | 5/2008 | Shah et al. | 600/220 |
| 2009/0069634 A1 | * | 3/2009 | Larkin | 600/222 |
| 2009/0203968 A1 | | 8/2009 | Winslow | |

* cited by examiner

*Primary Examiner* — David Bates
(74) *Attorney, Agent, or Firm* — J. Bennett Mullinax, LLC

(57) ABSTRACT

A vaginal speculum is provided that has an upper arm with a handle and jaw. A cross-sectional shape of a longitudinally extending portion may be constant along its entire longitudinal length so that the height of the portion is likewise constant along its length. Right and left side flanges may extend downward from the longitudinally extending portion and a tip of the jaw. The distance between the outer surfaces of the right and left side flanges in the lateral direction may be constant along their entire lengths in the longitudinal direction. A lower arm with a jaw and handle may be included and arranged with the upper arm so that their relative position to one another can be modified.

19 Claims, 6 Drawing Sheets

VAGINAL SPECULUM

FIELD OF THE INVENTION

The present invention relates generally to a vaginal speculum used to dilate the passage through the vagina for gynecological examination, treatment, or sampling. More particularly, the present application involves a vaginal speculum with upper and lower arms shaped and arranged with respect to one another to achieve enhanced patient comfort and health care provider visibility during use.

BACKGROUND

Vaginal specula typically include a pair of angled arms that are pivoted with respect to one another to form a set of jaws at one end and a handle on an opposite end. The handle can be squeezed by the health care provider to separate the set of jaws. The jaws are placed into the closed state upon insertion into the vagina, and the health care provider may subsequently open the jaws an amount necessary to cause the passageway to be sufficiently enlarged. A locking mechanism such as a ratchet arrangement or a pin can be used to lock the pivotal position of the upper and lower arms with respect to one another.

It is possible that once inserted and opened, vaginal tissue making up the lateral walls of the vagina will bulge between the jaws and obstruct the view or hinder the procedure conducted by the health care provider. Although this extra vaginal tissue may be present in all women, it may be more prevalent and problematic in women that are obese or who have been pregnant and have had multiple vaginal deliveries. In order to prevent or minimize this problem, the health care provider may apply additional pressure to the handle to further distend the walls of the vagina to force the tissue bulging into the jaws therefrom. This excessive distension of the vaginal tissue may be uncomfortable for the patient. Certain arrangements have been proposed to prevent tissue from entering the jaws during use. For example, one such arrangement proposes the use of a flexible membrane attached to the sides of the upper and lower arm to prevent vaginal tissue from bulging into the jaws during use.

Vaginal specula are designed in order to be retained within the vagina during times in which the vaginal muscles contract involuntarily. For example, it may be the case that a fit of coughing will cause the vaginal muscles to contract thus causing the inserted vaginal speculum to be ejected from the vagina. To prevent this from happening, the upper and lower arms include both convex and concave outer surfaces when viewed from the side of the arms and when viewed from the tops and bottoms of the arms that function to anchor the vaginal speculum in place once inserted and opened. The convex and concave shapes of the outer surfaces of the arms are also provided in order to exert minimal pressure on the urethra of the patient during use. Although suitable for their intended purpose, such vaginal specula may not provide for optimum patient comfort and health care provider access and observance during use. As such, there remains room for variation and improvement in the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which.

Figure 1:
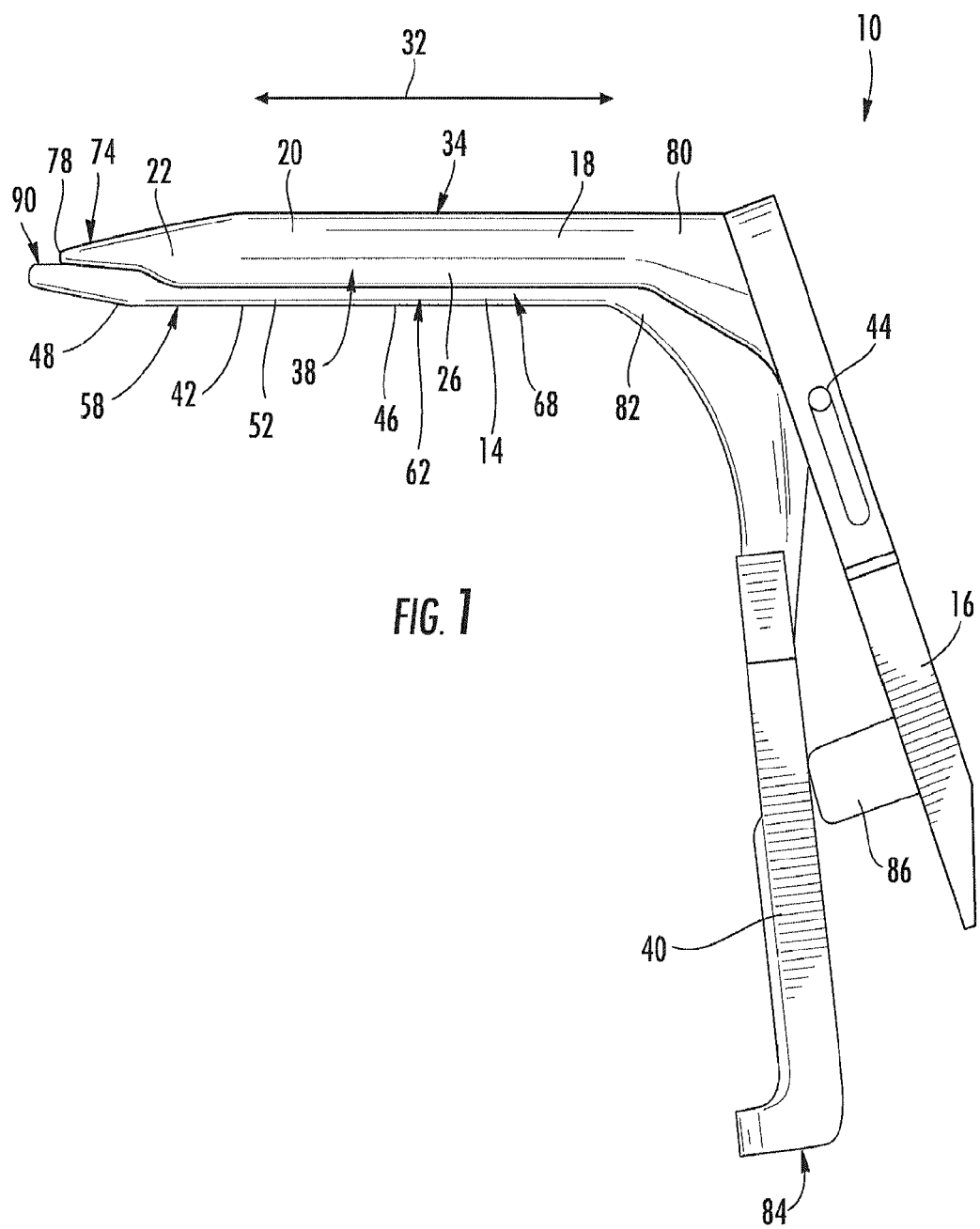
FIG. 1 is a side view of a vaginal speculum in a closed position in accordance with one exemplary embodiment.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5. Also, as used herein the term "proximal" refers to the direction generally towards the health care provider during a procedure, while the term "distal" refers to the direction generally away from the health care provider during a procedure.

The present invention provides for a vaginal speculum 10 for gynecological examination, treatment, and/or sampling. The vaginal speculum 10 includes a pair of arms 12 and 14 whose position relative to one another may be modified. For example, a pivot 44 may be used to place the arms 12 and 14 into pivoting engagement with one another. The arms 12 and 14 may be made so as to slide relative to one another so that their orientation to one another can be further adjusted as desired to increase or decrease the resulting distance between the arms 12 and 14. A locking mechanism 86 may be present in order to lock the relative position of the arms 12 and 14 to one another or to otherwise limit the orientation of the arms 12 and 14 to one another. Once inserted and properly oriented in the patient, observations or items may be made or passed through an aperture 88 in the upper arm 12. The jaws 18 and 42 of the upper arm 12 and lower arm 14 may be configured in a manner that allows for maximum patient comfort and health care provider observation and access.

Figure 2:
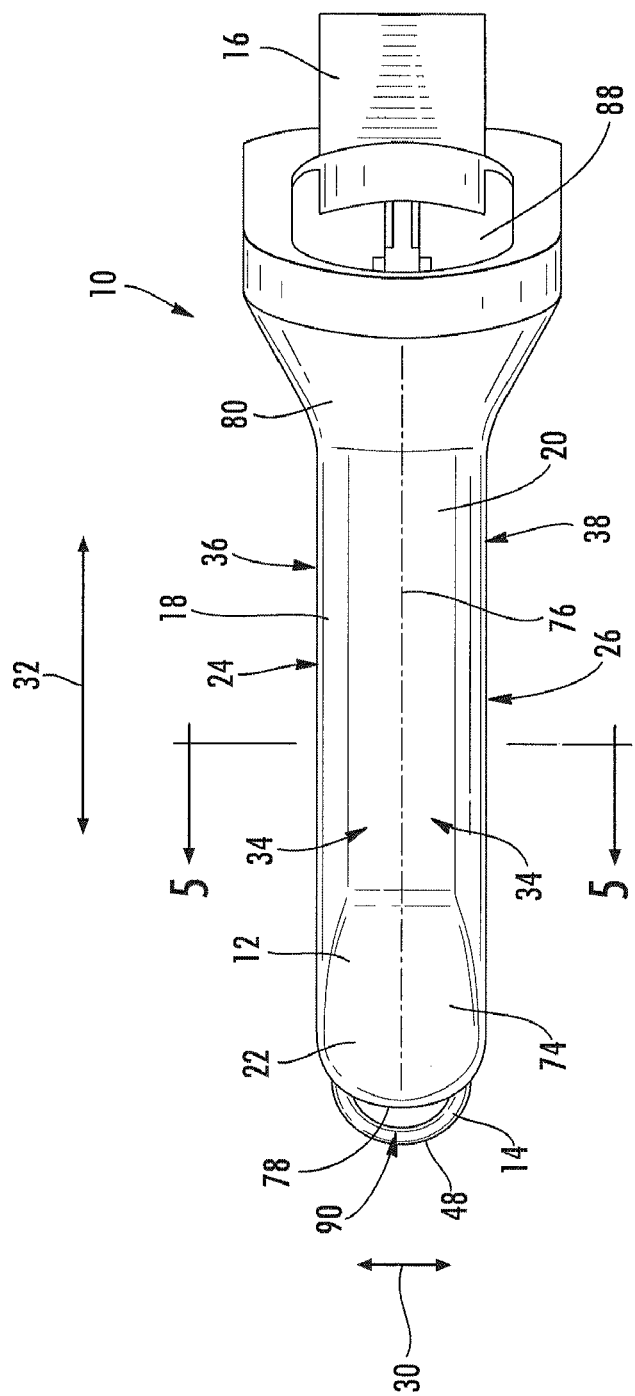
FIG. 2 is a top view of the vaginal speculum of FIG. 1.
Figure 3:
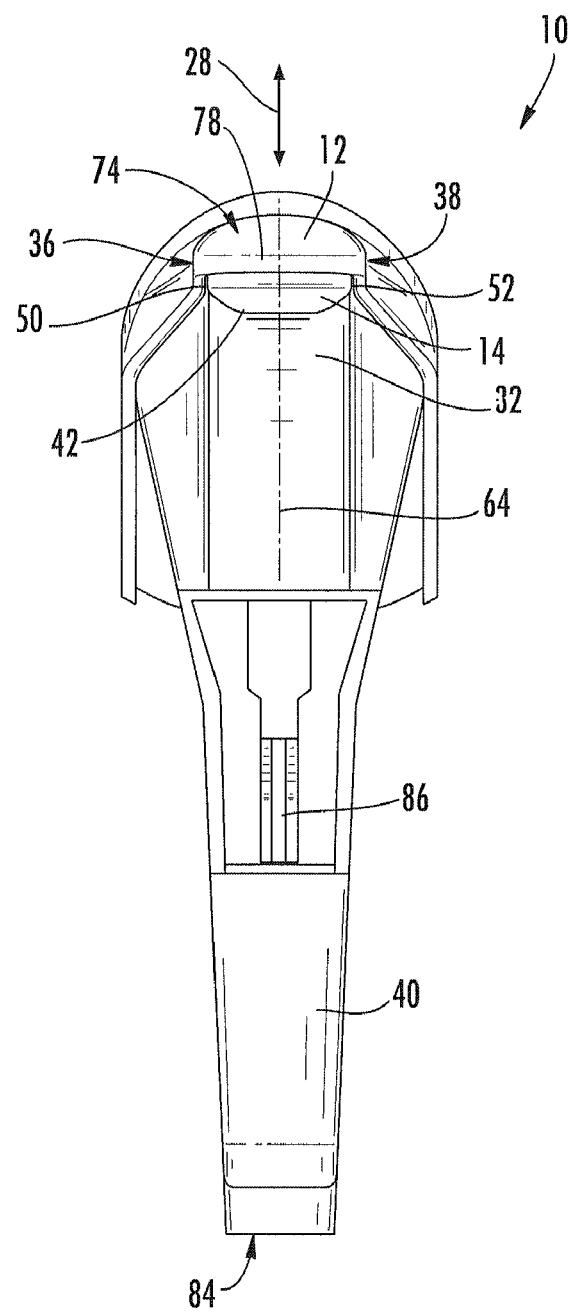
FIG. 3 is a front view of the vaginal speculum of FIG. 1.
Figure 4:
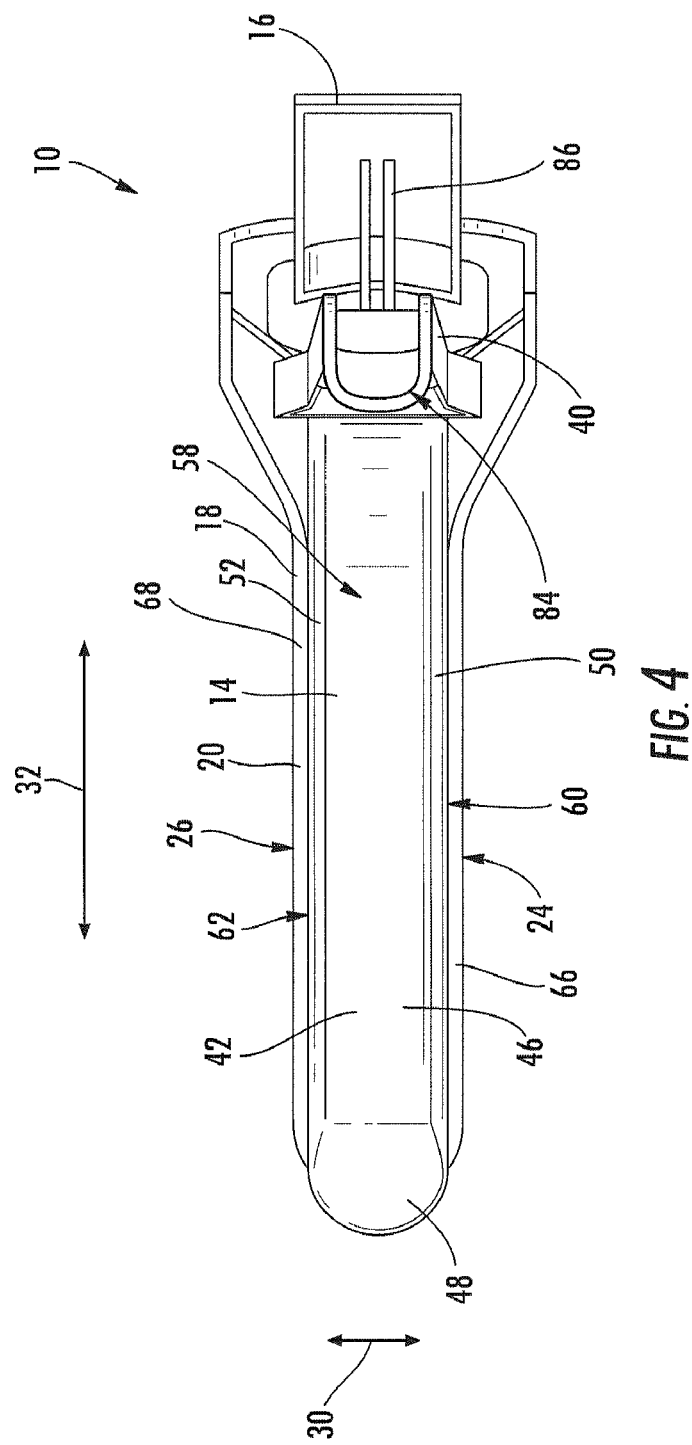
FIG. 4 is a bottom view of the vaginal speculum of FIG. 1.
Figure 5:
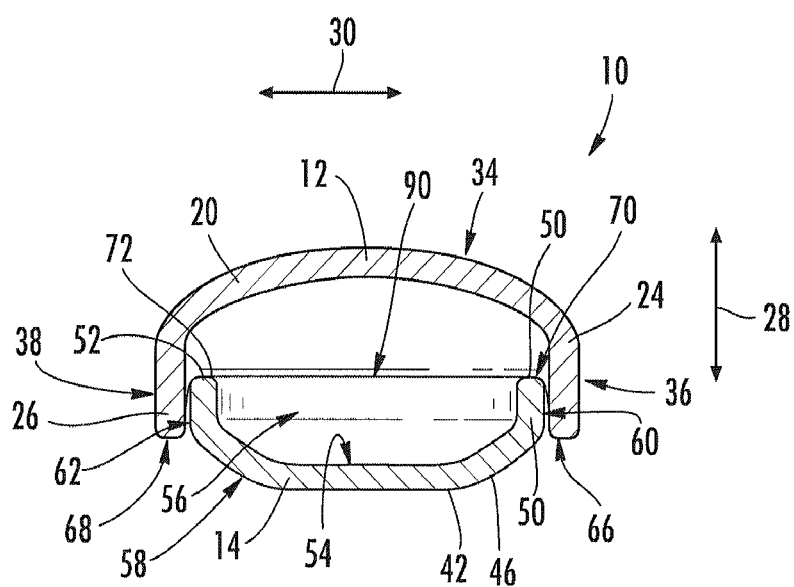
FIG. 5 is a cross-sectional view taken along line 5-5 of FIG. 2.
Figure 6:
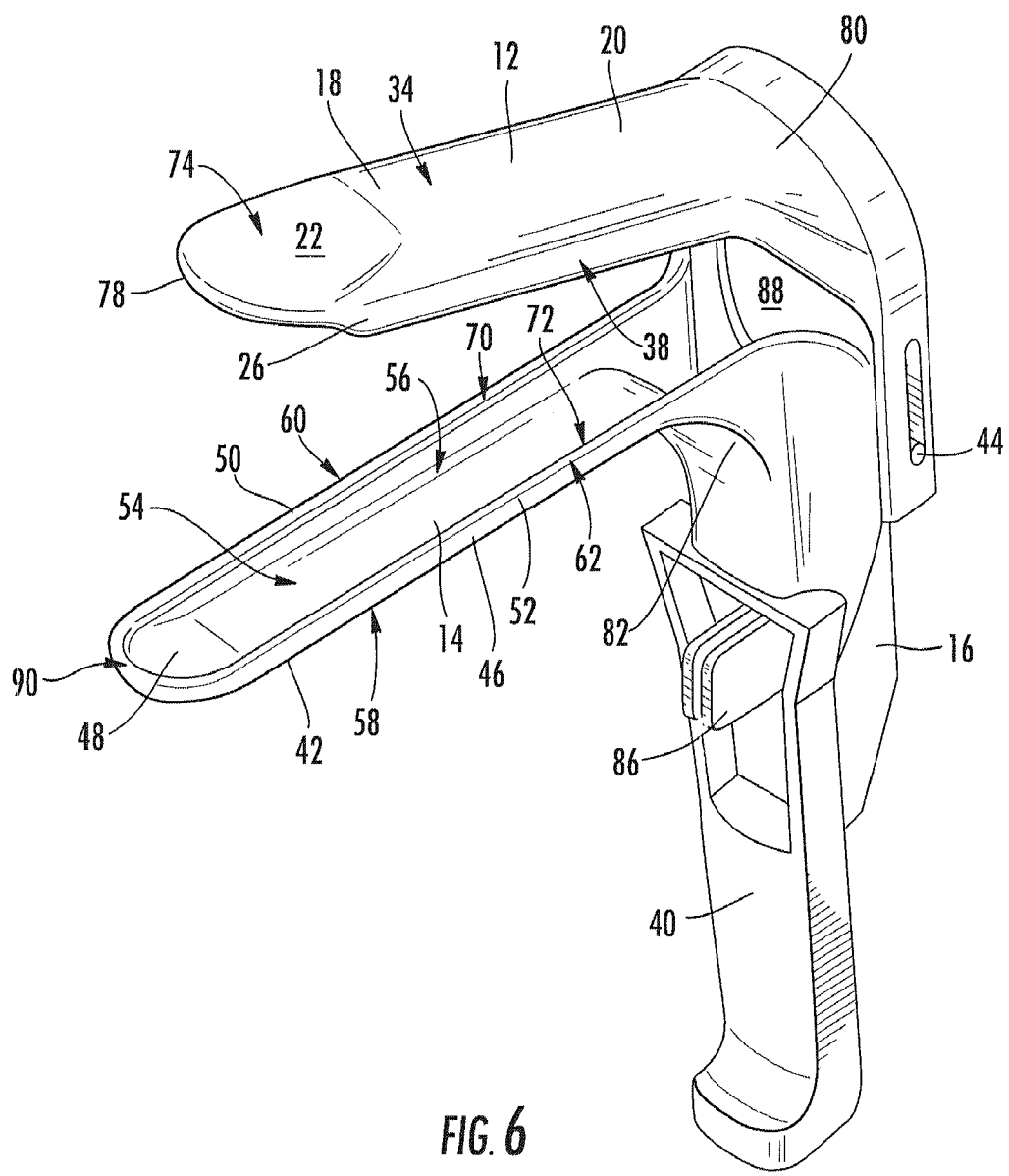
FIG. 6 is a side view of the vaginal speculum of FIG. 1 in an open position.

An exemplary embodiment of the vaginal speculum 10 is illustrated in FIGS. 1-6. The upper arm 12 includes a handle 16 and a jaw 18 that extends from a base 80. In a similar fashion, the lower arm 14 has a handle 40 and a jaw 42 that extends from a base 82. The jaw 18 of the upper arm 12 has a consistent distance in the lateral direction 30 upon extending from the base 80 until the tip 22 of the jaw 18 at which point the lateral distance decreases in the lateral direction 30. As such, the base 82 may have side walls that extend outwards in the lateral direction 30 in the direction away from the jaw 18. In use, a portion of the base 82 may be inserted within the vagina or may remain outside of the vagina.

The jaw 18 includes a longitudinally extending portion 20 that is connected to the base 80. The longitudinally extending portion 20 may be 7 centimeters long in the longitudinal direction 32 in accordance with certain exemplary embodiments. In other arrangements, the longitudinally extending portion 20 may be at least 6 centimeters long, from 5 to 7 centimeters long, or up to 9 centimeters long in the longitudinal direction 32. The longitudinally extending portion 20 may have a single, constant length in the lateral direction 30 along the entire length of the longitudinally extending portion 20 in the longitudinal direction 32. The distance in the lateral direction 30 may be up to 3 centimeters, up to 2.5 centimeters, or up to 2 centimeters in accordance with certain exemplary embodiments.

A tip 22 is also included on the jaw 18 and is located at the distal end of the longitudinally extending portion 20. The tip 22 has a constant distance in the lateral direction 30 along a portion of its longitudinal length that extends from the longitudinally extending portion 20. In certain exemplary embodiments, the tip 22 may have a constant distance in the lateral direction 30 along the first 2 centimeters of longitudinal length of the tip 22. In other arrangements, the tip 22 need not have a constant distance in the lateral direction 30 along any portion of its longitudinal length, or may have a constant distance in the lateral direction 30 from 1 centimeter to 3 centimeters, from 2 centimeters to 7 centimeters, or up to 10 centimeters in the longitudinal length of the tip 22. The length of the tip 22 in the lateral direction may diminish in the longitudinal direction 32 away from the longitudinally extending portion 20. The distal end 78 of the tip 22 may be curved in accordance with certain exemplary embodiments or may alternatively be straight in certain versions of the vaginal speculum 10.

A right side flange 24 and a left side flange 26 may extend from the longitudinally extending portion 20. The cross-sectional shape of the longitudinally extending portion 20 may remain the same along its entire length in the longitudinal direction 32 in certain embodiments. In other embodiments, the longitudinally extending portion 20 need not have a consistent cross-sectional shape along its longitudinal length. The outer surface 34 of the jaw 18 at the longitudinally extending portion 20 may be convex in shape upon extending in the lateral direction 30 from one side of the longitudinally extending portion 20 to the other. The outer surface 34 of the longitudinally extending portion 20 need not have a single convex shape but may be more convex nearer the flanges 24 and 26 and less convex in the center near the lateral midline 76 of the jaw 18. In certain embodiments, the outer surface 34 is not convex in shape but may be flat either across its entire length in the lateral direction 30 or along a portion of its length in the lateral direction 30.

The right side flange 24 may have an outer planar surface 36, and the left side flange 26 may have an outer planar surface 38. The outer planar surfaces 36 and 38 may be flat in that they have no convex or concave portions and are flat along their entire longitudinal lengths. The surfaces 36 and 38 may be parallel with one another and may be spaced a distance of 2.75 centimeters from one another in certain embodiments. The right and left side flanges 24 and 26 may extend a distance of 0.5 centimeters in the height direction 28 in certain embodiments. In this regard, the outer planar surfaces 36 and 38 may have a height of 0.5 centimeters. However, it is to be understood that other arrangements are possible in which the height of the outer planar surfaces 36 and 38 are different. For example, the outer planar surfaces 36 and 38 may be up to 0.5 centimeters, up to 1 centimeter, up to 1.5 centimeters, up to 2 centimeters, or from 1 to 5 centimeters in accordance with certain exemplary embodiments. The height of the outer planar surfaces 36 and 38 may be constant along the entire portion of the right and left side flanges 24 and 26 that are located below the longitudinally extending portion 20 along the entire longitudinal length of the longitudinally extending portion 20.

The outer planar surfaces 36 and 38 of the flanges 24 and 26 may extend from the ends of the longitudinally extending portion 20 that are convex in shape. As such, the outer surface 34 extending along the flanges 24 and 26 and portion 20 laterally may be convex everywhere other than along the outer planar surfaces 36 and 38. In other arrangements, a portion of the outer surface 34 may be flat at the longitudinally extending portion 20 adjacent the outer planar surfaces 36 and 38. The outer planar surfaces 36 and 38 below/adjacent the longitudinally extending portion 20 may be flat along the entire length of the longitudinally extending portion 20 in the longitudinal direction 32. As such, the combined outer surface 34 of the longitudinally extending portion 20, right side flange 24, and left side flange 26 may have a single consistent shape along the distance of the longitudinally extending portion 20 and adjacent flange sections 20 and 24 in the longitudinal direction 32.

The right side flange 24 may have a planar bottom surface 66, and the left side flange 26 may have a planar bottom surface 68. The planar bottom surfaces 66 and 68 may be angled to one another or may lie in the same plane as one another. The bottom surfaces 66 and 68 do not have a convex or concave shape extending in the longitudinal direction 32 but are instead planar surfaces in certain embodiments. In other embodiments, the bottom surfaces 66 and 68 need not be planar but may have some convex or concave shape at some point or along their entire longitudinal lengths.

The tip 22 is located at the end of the longitudinally extending portion 20 and has an outer surface 74 that extends downward in the height direction 28 away from the uppermost point of the longitudinally extending portion 20. The outer surface 74 extends to the distal end 78 of the tip 22. The outer surface 74 extends at a single, constant angle to the outer surface 34 of the longitudinally extending portion 20 along a lateral midline 76 of the jaw 18 in one embodiment. The outer surface 74 may be convex in shape in the lateral direction 30.

The right and left side flanges 24 and 26 may extend into the tip 22 so that a portion of the right and left side flanges 24 and 26 do not lie below the longitudinally extending portion 20 but rather lie below a portion of the tip 22. The right and left side flanges 24 and 26 may extend 2 centimeters, from 1 to 4 centimeters, from 0.5 centimeters to 10 centimeters, or up to 15 centimeters in the longitudinal direction 32 below the tip 22 in certain embodiments. The portions of the right and left side flanges 24 and 26 adjacent to the portions below the longitudinally extending portion 20 may be configured in an identical manner to the portions below the longitudinally extending portion 20. This identical configuration may extend a length of 1 centimeter, from 1 to 3 centimeters, or up to 5 centimeters in the longitudinal direction 32 in certain exemplary embodiments. As such, the right and left side flanges 24 and 26 may include outer planar surfaces 36 and 38 and planar bottom surfaces 66 and 68 that are the same under both the longitudinally extending portion 20 and a portion of the tip 22. Further, the heights of the right and left side flanges 24 and 26 along this portion of the tip 22 may be the same as the heights of the right and left side flanges 24 and 26 that are under the longitudinally extending portion 20. As such, the right and left side flanges 24 and 26 extend as uniform components having the same size and shape in the longitudinal direction 32 under both the longitudinally extending portion 20 and a portion of the tip 22.

Under the tip 22, the size and shape of the right and left side flanges 24 and 26 changes from that present under the longitudinally extending portion 20 and a portion of the tip 22. As shown, the height of the right and left side flanges 24 and 26 diminishes in the longitudinal direction 32. The bottom surfaces 66 and 68 may each have a portion that is convex in shape and one that is concave in shape under the tip 22.

The right and left side flanges 24 and 26 can be mirror images of one another with respect to the lateral midline 76. The jaw 18 may have a thickness of 2 millimeters in certain embodiments. In other embodiments, the thickness of the jaw 18 may be from 0.25 millimeters to 4 millimeters. The jaw 18 may be a single, integral piece so that the longitudinally extending portion 20, tip 22, right side flange 24, and left side flange 26 are formed into a single, unitary component. The longitudinally extending portion 46 may have a height of 0.5 centimeters, and the right and left side flanges 24 and 26 may have a height of 0.5 centimeters so that the height of the jaw 18 at this portion of the vaginal speculum 10 is 1 centimeter. The various heights may be changed in other embodiments. Applicant has unexpectedly discovered that the incorporation of right and left side flanges 24 and 26 provides for maximum patient comfort and still prevents excess vaginal tissue from bulging between the jaws 18 and 42 to disrupt viewing or hinder procedures during use of the vaginal speculum 10. The jaws 18 and 42 may thus not be connected to one another but may be capable of being placed into contact with one another. A membrane or other connection between the flanges 24 and 26 or any other portion of the jaw 18 with any portion of the jaw 42 need not be present. Connection between the arms 12 and 14 may thus be effected at a location proximal to the bases 80 and 82 such as at the pivot 44 or at the locking mechanism 86. The overall height of the jaw 18 and jaw 42 as measured from the very bottom portion of the jaw 42 on the outer surface 58 to the very top portion of the jaw 18 on the outer surface 34 may be 14.9 centimeters when the jaws 18 and 42 are in the closed position with the jaw 18 resting against the upper surfaces 70, 72, and 90 of the jaw 42. In other arrangements, this distance may be from 10-15 centimeters, from 5-20 centimeters, from 12-15 centimeters, from 14-17 centimeters, or up to 30 centimeters.

The lower arm 14 has a handle 40 and attached jaw 42. The jaw 42 extends distally in the longitudinal direction 32 away from the base 82. The jaw 42 includes a longitudinally extending portion 46 and a tip 48 located at the end of the longitudinally extending portion 46. A right side flange 50 and a left side flange 52 are located at the top of the longitudinally extending portion 46. The outer surface of the jaw 42 at the longitudinally extending portion 46 is convex from one end to the other in the lateral direction 30. The longitudinally extending portion 46 may have the same cross-sectional shape upon extending from the base 82 to the tip 48 in the longitudinal direction 32. The base 82 may be the portion of the lower arm 14 that extends in the lateral direction 30 proximally from the longitudinally extending portion 46, and the longitudinally extending portion 46 may have a single, constant distance in the lateral direction 30 along its entire length in the longitudinal direction 32.

The right and left side flanges 50 and 52 may have outer planar surfaces 60 and 62 that have a single, consistent size and shape extending above the entire longitudinally extending portion 46. As such, the height of the flanges 50 and 52 may be constant extending along and above the entire longitudinally extending portion 46. The outer planar surfaces 60 and 62 may be parallel to one another or can be oriented at an angle to one another in certain embodiments. Further, the outer planar surfaces 60 and 62 may be flat surfaces or can have convex or concave portions in various versions of the vaginal speculum 10. The right and left side flanges 50 and 52 may be mirror images of one another and may have a height of 2 millimeters, from 1 to 5 millimeters, or up to 10 millimeters in accordance with certain exemplary embodiments.

The longitudinally extending portion 46 may have a length of 8 centimeters in the longitudinal direction 32 in one exemplary embodiment. In other exemplary embodiments, the length may be from 3 to 9 centimeters, from 5 to 10 centimeters, or up to 20 centimeters. The jaw 42 may extend a longer distance in the longitudinal direction 32 than the jaw 18. The tip 48 can be arranged in a shape in the same manner as that described above with respect to the tip 22. The right and left side flanges 50 and 52 may extend above a portion of the tip 48 and be sized and configured in a manner identical to that of the portion of the right and left side flanges 50 and 52 located above the longitudinally extending portion 46. Further, the outer surface 58 of the tip 48 may extend at a single, constant angle from the outer surface 58 of the longitudinally extending portion 46 along the lateral midline of the jaw 42. As shown, the outer surfaces 60 and 62 of the right and left side flanges 50 and 52 do not have a convex and concave portion but are instead planar. Also, it should be noted that although the shape and configuration may or may not be mirror images, the sizes of the components between the jaws 18 and 42 need not be identical. The distance between the right and left side flanges 50 and 52 may be less than the distance between the right and left side flanges 24 and 26 in the lateral direction 30. As such, the longitudinally extending portion 46 and the tip 48 have a distance in the lateral direction 30 that is less than the longitudinally extending portion 20 and tip 22. As such, the jaw 42 may fit within the jaw 18 in certain arrangements of the vaginal speculum 10 at certain orientations of pivoting between the jaws 18 and 42.

The right and left side flanges 50 and 52 may have planar upper surfaces 70 and 72 that can be flat and planar along the entire longitudinal lengths of the right and left side flanges 50 and 52. The tip 48 may have an upper surface 90, and the upper surfaces 70, 72 and 90 may all be located at the same distance from the bottom surface 84 of the handle 40 in the height direction 28. As such, the entire upper surface of the jaw 42 can have a single, uniform height and configuration. The inner surfaces 54 of the longitudinally extending portion 46, tip 48, right side flange 50 and left side flange 52 may define a cavity 56 within the jaw 42. The upper arm 12 and lower arm 14 can be arranged so that the tip 22 cannot be inserted into the cavity 56.

The heights of the flanges 24 and 26 may be greater than the heights of the flanges 50 and 52. In certain embodiments, the height of the longitudinally extending portion 46 and the flanges 50 and 52 may be 5 millimeters. In other embodiments, the height of portion 46 and flanges 50 and 52 may be from 2 millimeters to 7 millimeters, from 5 millimeters to 10 millimeters, or up to 15 millimeters. The combined height of the longitudinally extending portion 20 and flanges 24 and 26 may be greater than the combined height of the longitudinally extending portion 46 and flanges 50 and 52 in accordance with certain exemplary embodiments.

The jaw 42 may have a thickness of 2 millimeters in certain exemplary embodiments. In other embodiments, the jaw 42 may have a thickness from 1 to 3 millimeters, from 2 to 3.5 millimeters, or up to 5 millimeters. The various portions of the jaw 42 such as the longitudinally extending portion 46, tip 48, right side flange 50 and left side flange 52 can be made of a single integral piece or may be separate components that are formed and subsequently attached to one another. The upper and lower arms 12 and 14 may be made out of any suitable material. For example, the arms 12 and 14 may be made of polystyrene, polypropylene, or poly vinyl chloride in accordance with certain exemplary embodiments.

In accordance with certain exemplary embodiments of the vaginal speculum 10, the length of the jaw 18 in the longitudinal direction 32 is 10 centimeters of which the longitudinally extending portion 20 is 7 centimeters in length and the tip 22 is 3 centimeters in length. The length of the jaw 42 in the longitudinal direction 32 is also 10 centimeters of which the length of the longitudinally extending portion 46 is 8 centimeters and the length of the tip 48 is 2 centimeters. The jaw 42 of the lower arm 14 may extend a greater distance in the longitudinal direction 32 than the jaw 18 of the upper arm 12. However, it is to be understood that other arrangements are possible in which the jaw 42 extends a shorter distance in the longitudinal direction 32 than the jaw 18, and other versions exist in which the jaws 18 and 42 extend the same distance in the longitudinal direction 32.

The vaginal speculum 10 can be used as a medium vaginal speculum 10. However, the upper arm 12 and lower arm 14 may be adjusted in order to make the vaginal speculum 10 comparable with a large vaginal speculum. In this regard, a slot is provided through which the pivot 44 may ride so that the height of the upper arm 12 can be raised relative to the height of the lower arm 14. The distance between the upper and lower arms 12 and 14 may therefore be increased so that the instrument may be used as a large vaginal speculum. However, it is to be understood that this adjustability need not be present in other versions of the vaginal speculum 10.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A vaginal speculum, comprising:
   an upper arm having a handle and a jaw, wherein the jaw of the upper arm has a longitudinally extending portion that extends in a longitudinal direction and a tip located distally of the longitudinally extending portion, wherein the jaw of the upper arm has a right side flange and a left side flange that extend downward in a height direction from the longitudinally extending portion and the tip of the jaw of the upper arm, wherein the right side and left side flanges of the jaw of the upper arm each have an outer surface that is planar that extends in the longitudinal direction below and along the majority of the longitudinal length of the longitudinally extending portion and that extends in the longitudinal direction below and along a portion of the longitudinal length of the tip of the jaw of the upper arm with the outer planar surfaces of the right side flange and the left side flange of the jaw of the upper arm having a constant height over the longitudinally extending portion and at least a portion of the tip of the jaw of the upper arm; and
   a lower arm having a handle and a jaw, the jaw of the lower arm having a longitudinally extending portion that extends in the longitudinal direction and a tip located distally of the longitudinally extending portion of the jaw of the lower arm and the jaw of the lower arm having a right side flange and a left side flange that extend upward in the height direction from the longitudinally extending portion and the tip of the jaw of the lower arm with the longitudinally extending portion, the tip, the right side flange, and the left side flange of the jaw of the lower arm having inner surfaces that define a cavity of the jaw of the lower arm, wherein the relative position between the upper arm and the lower arm can be modified to modify the orientation between the jaw of the upper arm and the jaw of the lower arm;
   wherein the left side flange of the jaw of the upper arm is integrally formed with the longitudinally extending portion of the jaw of the upper arm and wherein the relative position between the left side flange and the longitudinally extending portion of the jaw of the upper arm remains the same when the relative position between the upper arm and the lower arm is modified;
   wherein the longitudinally extending portion and the tip of the jaw of the lower arm together have a length in the longitudinal direction that is greater than a length in the longitudinal direction of both the longitudinally extending portion and tip of the jaw of the upper arm such that the tip of the jaw of the lower arm extends further in the longitudinal direction than the tip of the jaw of the upper arm when the jaws of the upper and lower arms are in a closed position; and
   wherein the longitudinally extending portion and the tip of the jaw of the lower arm have a distance in the lateral direction that is less than a distance in the lateral direction of the longitudinally extending portion and the tip of the jaw of the upper arm such that the outer planar surfaces of the right and left flanges of the longitudinally extending portion and the tip of the jaw of the upper arm extend around at least an upper portion of the right and left flanges of the longitudinally extending portion and the tip of the jaw of the lower arm when the jaws of the upper and lower arms are in a closed position thereby the jaw of the lower arm fitting within at least a portion of the longitudinally extending portion and the tip of the jaw of the upper arm with no portion of the jaw of the upper arm being capable of being positioned within the cavity of the jaw of the lower arm when the jaws of the upper and lower arms are in the closed position.

2. The vaginal speculum as set forth in claim 1, wherein the outer planar surface of the right side flange of the jaw of the upper arm extends in the longitudinal direction along the entire longitudinal length of the longitudinally extending portion, and wherein the outer planar surface of the left side flange of the jaw of the upper arm extends in the longitudinal direction along the entire longitudinal length of the longitudinally extending portion.

3. The vaginal speculum as set forth in claim 1, wherein the longitudinally extending portion extends at least six centimeters in the longitudinal direction, and wherein the tip extends at least two centimeters in the longitudinal direction.

4. The vaginal speculum as set forth in claim 1, wherein the upper arm and lower arm are in pivotal engagement with one another so that their relative position to one another can be modified in order to modify the orientation between the jaw of the upper arm and the jaw of the lower arm angularly.

5. The vaginal speculum as set forth in claim 1, wherein the right side and left side flanges of the jaw of the lower arm each have an outer surface that is planar that extends in the longitudinal direction above and along the majority of the longitudinal length of the longitudinally extending portion of the jaw of the lower arm and that extends in the longitudinal direction above and along a portion of the longitudinal length of the tip of the jaw of the lower arm, wherein a lateral distance between the outer planar surfaces of the right and left side flanges of the jaw of the upper arm is greater than a lateral distance between the outer planar surfaces of the right and left side flanges of the jaw of the lower arm.

6. The vaginal speculum as set forth in claim 5, wherein the right side flange and the left side flange of the jaw of the upper arm each have a planar bottom surface that extend in the longitudinal direction below and along the majority of the longitudinal length of the longitudinally extending portion and that extend in the longitudinal direction below and along a portion of the longitudinal length of the tip of the jaw of the upper arm, and wherein the right side flange and the left side flange of the jaw of the lower arm each have a planar upper surface that extend in the longitudinal direction above and along the majority of the longitudinal length of the longitudinally extending portion and that extend in the longitudinal direction above and along a portion of the longitudinal length of the tip of the jaw of the lower arm.

7. The vaginal speculum as set forth in claim 1, wherein the cross-sectional shape of the longitudinally extending portion of the jaw of the upper arm is constant along the entire longitudinal length of the longitudinally extending portion of the jaw of the upper arm such that the height of the longitudinally extending portion of the jaw of the upper arm is constant along the entire longitudinal length of the longitudinally extending portion of the jaw of the upper arm, wherein the outer surface of the longitudinally extending portion of the jaw of the upper arm is convex in shape along a lateral length of the longitudinally extending portion of the jaw of the upper arm, wherein the distance between the outer surface of the right side flange of the jaw of the upper arm and the outer surface of the left side flange of the jaw of the upper arm in a lateral direction is constant along the entire longitudinal lengths of the right side flange and the left side flange of the jaw of the upper arm.

8. The vaginal speculum as set forth in claim 1, wherein the tip of the jaw of the upper arm has an outer surface extending from the longitudinally extending portion of the jaw of the upper arm to the distal end of the tip, the outer surface of the tip of the jaw of the upper arm extending along at a single constant angle relative to the outer surface of the longitudinally extending portion of the jaw of the upper arm along a lateral midline of the longitudinally extending portion of the jaw of the upper arm.

9. The vaginal speculum as set forth in claim 1, wherein the jaw of the lower arm fits within the jaw of the upper arm at certain orientations of pivoting between the jaws of the lower and upper arms.

10. A vaginal speculum, comprising:
an upper arm having a handle and a jaw, wherein the jaw of the upper arm has a base and a longitudinally extending portion that extends distally from the base in a longitudinal direction and a tip that extends distally from the longitudinally extending portion, wherein the cross-sectional shape of the longitudinally extending portion of the jaw of the upper arm is constant along the entire longitudinal length of the longitudinally extending portion of the jaw of the upper arm such that a height of the longitudinally extending portion of the jaw of the upper arm is constant along the entire longitudinal length of the longitudinally extending portion of the jaw of the upper arm, wherein the outer surface of the longitudinally extending portion of the jaw of the upper arm is convex in shape along a lateral length of the longitudinally extending portion of the jaw of the upper arm, wherein the jaw of the upper arm has a right side flange and a left side flange that extend downward in a height direction from the longitudinally extending portion and the tip of the jaw of the upper arm, wherein a distance between an outer surface of the right side flange and an outer surface of the left side flange in a lateral direction is constant along the entire longitudinal lengths of the right side flange and the left side flange of the jaw of the upper arm, wherein the right side and left side flanges of the jaw of the upper arm each have an outer surface that is planar that extends in the longitudinal direction below and along the majority of the longitudinal length of the longitudinally extending portion and that extends in the longitudinal direction below and along a portion of the longitudinal length of the tip of the jaw of the upper arm with the outer planar surfaces of the right side flange and the left side flange of the jaw of the upper arm having a constant height over the longitudinally extending portion and at least a portion of the tip of the jaw of the upper arm; and a lower arm having a handle and a jaw, the jaw of the lower arm having a longitudinally extending portion that extends in the longitudinal direction and a tip that extends distally from the longitudinally extending portion of the jaw of the lower arm and the jaw of the lower arm having a right side flange and a left side flange that extend upward in the height direction from the longitudinally extending portion and the tip of the jaw of the lower arm with the longitudinally extending portion, the tip, the right side flange, and the left side flange of the jaw of the lower arm having inner surfaces that define a cavity of the jaw of the lower arm, wherein the relative position between the upper arm and the lower arm can be modified to modify the orientation between the jaw of the upper arm and the jaw of the lower arm;

wherein the longitudinally extending portion and the tip of the jaw of the lower arm together have a length in the longitudinal direction that is greater than a length in the longitudinal direction of both the longitudinally extending portion and tip of the jaw of the upper arm such that the tip of the jaw of the lower arm extends further in the longitudinal direction than the tip of the jaw of the upper arm when the jaws of the upper and lower arms are in a closed position; and wherein the longitudinally extending portion and the tip of the jaw of the lower arm have a distance in the lateral direction that is less than a distance in the lateral direction of the longitudinally extending portion and the tip of the jaw of the upper arm such that the outer planar surfaces of the right and left flanges of the longitudinally extending portion and the tip of the jaw of the upper arm extend around at least an upper portion of the right and left flanges of the longitudinally extending portion and the tip of the jaw of the lower arm when the jaws of the upper and lower arms are in a closed position thereby the jaw of the lower arm fitting within at least a portion of the longitudinally extending portion and the tip of the jaw of the upper arm with no portion of the jaw of the upper arm being capable of being positioned within the cavity of the jaw of the lower arm when the jaws of the upper and lower arms are in the closed position.

11. The vaginal speculum as set forth in claim 10, wherein the jaw of the lower arm has a base with the longitudinally extending portion that extends distally from the base, wherein the cross-sectional shape of the longitudinally extending portion of the jaw of the lower arm is constant along the entire longitudinal length of the longitudinally extending portion of the jaw of the lower arm such that the height of the longitudinally extending portion of the jaw of the lower arm is constant along the entire longitudinal length of the longitudinally extending portion of the jaw of the lower arm, wherein the outer surface of the longitudinally extending portion of the jaw of the lower arm is convex in shape along the lateral length of the longitudinally extending portion of the jaw of the lower arm, wherein a distance between an outer surface of the right side flange and an outer surface of the left side flange in the lateral direction is constant along the entire longitudinal lengths of the right side flange and the left side flange of the jaw of the lower arm.

12. The vaginal speculum as set forth in claim 11, wherein the upper arm and lower arm are in pivotal engagement with one another so that their relative position to one another can be modified in order to modify the orientation between the jaw of the upper arm and the jaw of the lower arm angularly.

13. The vaginal speculum as set forth in claim 11, wherein the distance in the lateral direction between the outer surfaces of the right and left side flanges of the jaw of the upper arm is greater than the distance in the lateral direction between the outer surfaces of the right and left side flanges of the jaw of the lower arm.

14. The vaginal speculum as set forth in claim 10, wherein the height of the right side flange and the height of the left side flange below the entire longitudinally extending portion and below a portion of the tip of the jaw of the upper arm are constant.

15. The vaginal speculum as set forth in claim 10, wherein the distance in the height direction between a bottom surface of the handle of the lower arm and an upper surface of the tip of the jaw of the upper arm, the right side flange and the left side flange of the jaw of the lower arm is constant along the entire longitudinal lengths of the upper surface of the tip, the right side flange and the left side flange of the jaw of the lower arm.

16. The vaginal speculum as set faith in claim 10, wherein the longitudinally extending portion extends at least six centimeters in the longitudinal direction, and wherein the tip extends at least two centimeters in the longitudinal direction.

17. The vaginal speculum as set forth in claim 10, wherein the tip of the jaw of the upper arm has an outer surface extending from the longitudinally extending portion of the jaw of the upper arm to the distal end of the tip, the outer surface of the tip of the jaw of the upper arm extending along at a single constant angle relative to the outer surface of the longitudinally extending portion of the jaw of the upper arm along a lateral midline of the longitudinally extending portion of the jaw of the upper arm.

18. The vaginal speculum as set forth in claim 10, wherein the relative position between the left side flange and the longitudinally extending portion remains the same when the relative position between the upper arm and the lower arm is modified.

19. A vaginal speculum, comprising:
an upper arm having a handle and a jaw, wherein the jaw of the upper arm has a base and a longitudinally extending portion that is at least six centimeters long in a longitudinal direction and extends distally from the base, and a tip that is at least two centimeters long in the longitudinal direction that extends distally from the longitudinally extending portion, wherein the cross-sectional shape of the longitudinally extending portion of the jaw of the upper arm is constant along the entire longitudinal length of the longitudinally extending portion of the jaw of the upper arm such that a height of the longitudinally extending portion of the jaw of the upper arm is constant along the entire longitudinal length of the longitudinally extending portion of the jaw of the upper arm, wherein the outer surface of the longitudinally extending portion of the jaw of the upper arm is convex in shape along a lateral length of the longitudinally extending portion of the jaw of the upper arm, wherein the jaw of the upper arm has a right side flange and a left side flange that extend downward in a height direction from the longitudinally extending portion and the tip of the jaw of the upper arm, wherein the right side and left side flanges of the jaw of the upper arm each have an outer surface that is planar that extends in the longitudinal direction below and along the majority of the longitudinal length of the longitudinally extending portion and that extends in the longitudinal direction below and along a portion of the longitudinal length of the tip of the jaw of the upper arm with the planar outer surfaces of the right side flange and the left side flange of the jaw of the upper arm having a constant height over the longitudinally extending portion and at least a portion of the tip of the jaw of the upper arm, wherein the distance between an outer surface of the right side flange and an outer surface of the left side flange in a lateral direction is constant along the entire longitudinal lengths of the right side flange and the left side flange of the jaw of the upper arm, wherein the tip of the jaw of the upper arm has an outer surface, wherein the outer surface of the tip of the jaw of the upper arm from the longitudinally extending portion of the jaw of the upper arm to the distal end of the tip is oriented at a single constant angle to the outer surface of the longitudinally extending portion of the jaw of the upper arm along a lateral midline of the longitudinally extending portion of the jaw of the upper arm; and a lower arm having a handle and a jaw, wherein the upper arm and lower arm are in pivotal engagement with one another, wherein the jaw of the lower arm has a base and a longitudinally extending portion that extends at least seven centimeters distally from the base and a tip that extends at least one centimeter distally from the longitudinally extending portion, wherein the cross-sectional shape of the longitudinally extending portion of the jaw of the lower arm is constant along the entire longitudinal length of the longitudinally extending portion of the jaw of the lower arm such that the height of the longitudinally extending portion of the jaw of the lower arm is constant along the entire longitudinal length of the longitudinally extending portion of the jaw of the lower arm, wherein the outer surface of the longitudinally extending portion of the jaw of the lower arm is convex in shape along the lateral length of the longitudinally extending portion of the jaw of the lower arm, wherein the jaw of the lower arm has a right side flange and a left side flange that extend upward in the height direction from the longitudinally extending portion and the tip of the jaw of the lower arm with the longitudinally extending portion, the tip, the right side flange, and the left side flange of the jaw of the lower arm having inner surfaces that define a cavity of the jaw of the lower arm, wherein the distance between an outer surface of the right side flange and an outer surface of the left side flange in the lateral direction is constant along the entire longitudinal lengths of the right side flange and the left side flange of the jaw of the lower arm, wherein the tip of the jaw of the lower arm has an outer surface, wherein the outer surface of the tip of the jaw of the lower arm along a lateral midline of the tip of the jaw of the lower arm from the longitudinally extending portion of the jaw of the lower arm to the distal end of the tip extends at a single constant angle relative to the outer surface of the longitudinally extending portion of the jaw of the lower arm along a lateral midline of the longitudinally extending portion of the jaw of the lower arm;

wherein the relative position between the left side flange and the longitudinally extending portion remains the same when the relative position between the upper arm and the lower arm is modified;

wherein the longitudinally extending portion and the tip of the jaw of the lower arm together have a length in the longitudinal direction that is greater than a length in the longitudinal direction of both the longitudinally extending portion and tip of the jaw of the upper arm such that the tip of the jaw of the lower arm extends further in the longitudinal direction than the tip of the jaw of the upper arm when the jaws of the upper and lower arms are in a closed position; and wherein the outer planar surfaces of the right and left flanges of the longitudinally extending portion and the tip of the jaw of the upper arm extend around at least a portion of the right and left flanges of the longitudinally extending portion and the tip of the jaw of the lower arm when the jaws of the upper and lower arms are in a closed position thereby the jaw of the lower arm fitting within at least a portion of the longitudinally extending portion and the tip of the jaw of the upper arm with no portion of the jaw of the upper arm being capable of being positioned within the cavity of the jaw of the lower arm when the jaws of the upper and lower arms are in the closed position.

* * * * *